United States Patent
Choi et al.

(10) Patent No.: US 10,174,133 B2
(45) Date of Patent: Jan. 8, 2019

(54) MODIFIED STYRENE-BUTADIENE COPOLYMER, PREPARATION METHOD THEREOF, AND RUBBER COMPOSITION INCLUDING THE SAME

(71) Applicant: LG Chem, Ltd., Seoul (KR)

(72) Inventors: Seung Ho Choi, Daejeon (KR); Min Soo Kim, Daejeon (KR); Cheol Jae Kim, Daejeon (KR); Won Mun Choi, Daejeon (KR)

(73) Assignee: LG Chem, Ltd. (KR)

( * ) Notice: Subject to any disclaimer, the term of this patent is extended or adjusted under 35 U.S.C. 154(b) by 76 days.

(21) Appl. No.: 15/324,815

(22) PCT Filed: Nov. 27, 2015

(86) PCT No.: PCT/KR2015/012821
§ 371 (c)(1),
(2) Date: Jan. 9, 2017

(87) PCT Pub. No.: WO2016/085285
PCT Pub. Date: Jun. 2, 2016

(65) Prior Publication Data
US 2017/0204205 A1   Jul. 20, 2017

(30) Foreign Application Priority Data

Nov. 28, 2014 (KR) .................. 10-2014-0168978
Dec. 4, 2014 (KR) .................. 10-2014-0172962
(Continued)

(51) Int. Cl.
*C08C 19/25* (2006.01)
*C07F 7/18* (2006.01)
(Continued)

(52) U.S. Cl.
CPC ............... *C08C 19/25* (2013.01); *B60C 1/00* (2013.01); *C07F 7/1804* (2013.01); *C08C 19/22* (2013.01);
(Continued)

(58) Field of Classification Search
None
See application file for complete search history.

(56) References Cited

U.S. PATENT DOCUMENTS 4,239,539 A * 12/1980 Ginsberg ............. C08K 5/5455
106/1.17
4,330,444 A * 5/1982 Pollman ................. C03C 25/26
428/378
(Continued)

FOREIGN PATENT DOCUMENTS

CN   104072816 A   10/2014
JP   H10657767 B2   8/1994
(Continued)

OTHER PUBLICATIONS

International Search Report from PCT/KR2015/012821, dated Mar. 22, 2016.
(Continued)

*Primary Examiner* — Robert S Loewe
(74) *Attorney, Agent, or Firm* — Lerner, David, Littenberg, Krumholz & Mentlik, LLP

(57) ABSTRACT

The present invention relates to a modified styrene-butadiene copolymer with a high modification ratio, including a functional group derived from a modifier represented by Formula 1, a preparation method thereof, a rubber composition including the same, and a tire manufactured from the rubber composition.

20 Claims, 1 Drawing Sheet

(30) Foreign Application Priority Data

Dec. 22, 2014 (KR) ........................ 10-2014-0186009
Nov. 26, 2015 (KR) ........................ 10-2015-0166690

(51) Int. Cl.

| | | |
|---|---|---|
| *C08F 236/10* | (2006.01) | |
| *B60C 1/00* | (2006.01) | |
| *C08F 36/04* | (2006.01) | |
| *C08C 19/22* | (2006.01) | |
| *C08C 19/26* | (2006.01) | |
| *C08F 212/08* | (2006.01) | |
| *C08F 4/46* | (2006.01) | |
| *C08F 4/48* | (2006.01) | |
| *C08F 236/06* | (2006.01) | |
| *C08K 3/04* | (2006.01) | |
| *C08K 3/36* | (2006.01) | |
| *C08L 9/00* | (2006.01) | |
| *C08L 9/06* | (2006.01) | |
| *C08L 15/00* | (2006.01) | |

(52) U.S. Cl.
CPC ............ *C08C 19/26* (2013.01); *C08F 4/46* (2013.01); *C08F 4/48* (2013.01); *C08F 36/04* (2013.01); *C08F 212/08* (2013.01); *C08F 236/06* (2013.01); *C08F 236/10* (2013.01); *C08K 3/04* (2013.01); *C08K 3/36* (2013.01); *C08L 9/00* (2013.01); *C08L 9/06* (2013.01); *C08L 15/00* (2013.01)

(56) References Cited

U.S. PATENT DOCUMENTS

| | | | | |
|---|---|---|---|---|
| 5,532,398 | A * | 7/1996 | Wolter | C07F 7/182 526/279 |
| 5,948,927 | A * | 9/1999 | Gunther | C07F 7/1836 556/418 |
| 6,228,496 | B1 * | 5/2001 | Lawton | C03C 25/321 428/378 |
| 2004/0167275 | A1 | 8/2004 | Okuhira et al. | |
| 2004/0254301 | A1 | 12/2004 | Tsukimawashi et al. | |
| 2005/0288415 | A1 * | 12/2005 | Beers | C08L 83/04 524/425 |
| 2012/0059121 | A1 * | 3/2012 | Backer | B60C 1/00 524/856 |
| 2013/0302627 | A1 | 11/2013 | Roehrig et al. | |
| 2013/0323519 | A1 * | 12/2013 | Klun | H01L 23/296 428/447 |
| 2014/0243476 | A1 | 8/2014 | Lee et al. | |
| 2014/0296421 | A1 | 10/2014 | Miyazaki | |
| 2014/0309370 | A1 | 10/2014 | Ostendorf et al. | |
| 2015/0221886 | A1 | 8/2015 | Klun et al. | |
| 2017/0066850 | A1 | 3/2017 | Lee et al. | |

FOREIGN PATENT DOCUMENTS

| | | | |
|---|---|---|---|
| JP | 2004210977 A | 7/2004 | |
| JP | 4176486 B2 | 11/2008 | |
| JP | 2013060525 A | 4/2013 | |
| JP | 2013082842 A | 5/2013 | |
| JP | 2013087210 A | 5/2013 | |
| JP | 2013087219 A | 5/2013 | |
| JP | 2014177517 A | 9/2014 | |
| JP | 2014177520 A | 9/2014 | |
| JP | 2014189774 A | 10/2014 | |
| JP | 2014534291 A | 12/2014 | |
| JP | 2015529580 A | 10/2015 | |
| JP | 2016014122 A | 1/2016 | |
| KR | 20130090811 A | 8/2013 | |
| KR | 20140122664 A | 10/2014 | |
| WO | 03029299 A1 | 4/2003 | |
| WO | WO-2012078469 A1 * | 6/2012 | ........... C08G 77/445 |
| WO | 2012106184 A2 | 8/2012 | |
| WO | 2014025348 A1 | 2/2014 | |

OTHER PUBLICATIONS

Database WPI, Week 201325, Thomson Scientific, London, GB; AN 2013-555395, XP002774695, 2017 Clarivate Analytics.
Database WPI, Week 201325, Thomson Scientific, London, GB; AN 2013-E55395, XP002774672, 2017 Clarivate Analytics.
Database WPI, Week 201334, Thomson Scientific, London, GB; AN 2013-H12432, XP002774673, 2017 Clarivate Analytics.
Database WPI, Week 201334, Thomson Scientific, London, GB; AN 2013-H12432, XP002774696, 2017 Clarivate Analytics.
Database WPI, Week 201335, Thomson Scientific, London, GB; AN 2013-H12439, XP002774674, 2017 Clarivate Analytics.
Database WPI, Week 201335, Thomson Scientific, London, GB; AN 2013-H12439, XP002774697, 2017 Clarivate Analytics.
Extended European Search Report for Application No. EP15863701.7 dated Nov. 7, 2017.
Extended European Search Report for Application No. EP15864093.8 dated Nov. 7, 2017.
International Search Report from PCT/KR2015/012818, dated Mar. 23, 2016.
Chinese Search Report for CN2015800480694 dated Jun. 4, 2018.
Eren, T. et al., Polymerization of Methacryl and Triethoxysilane Functionalized Stearate Ester: Titanium Dioxide Composite Films and Their Photocatalytic Degradations, Journal of Applied Polymer Science, Aug. 5, 2007, vol. 105, No. 3, pp. 1426-1436, XP055516029.
Schmider, M. et al., "A Versatile Synthetic Route to Phosphonate-Functional Monomers, Oligomers, Silanes, and Hybrid Nanoparticles", Macromolecules, Nov. 1, 2005, vol. 38, No. 23, pp. 9548-9555., XP055515524.

* cited by examiner

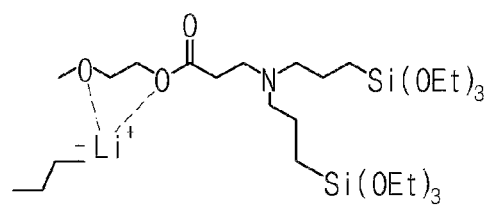

MODIFIED STYRENE-BUTADIENE COPOLYMER, PREPARATION METHOD THEREOF, AND RUBBER COMPOSITION INCLUDING THE SAME

The present application is a national phase entry under 35 U.S.C. § 371 of International Application No. PCT/KR2015/012821 filed Nov. 27, 2015, published in Korean, which claims priority from Korean Patent Application Nos. 10-2014-0168978, filed on Nov. 28, 2014, 10-2014-0172962, filed on Dec. 4, 2014, 10-2014-0186009, filed on Dec. 22, 2014, and 10-2015-0166690, filed on Nov. 26, 2015, all of which are incorporated herein by reference.

CROSS-REFERENCE TO RELATED APPLICATIONS

This application claims the benefits of priority based on Korean Patent Application Nos. 10-2014-0168978, filed on Nov. 28, 2014, 10-2014-0172962, filed on Dec. 4, 2014, 10-2014-0186009, filed on Dec. 22, 2014, and 10-2015-0166690, filed on Nov. 26, 2015, and the entire contents disclosed in the Korean patent applications are hereby incorporated as a part of the specification.

TECHNICAL FIELD

The present invention relates to a modified styrene-butadiene copolymer having a high modification ratio, a preparation method thereof, a rubber composition including the same, and a tire manufactured from the rubber composition.

BACKGROUND ART

Recently, according to the requirement of low fuel consumption in an automobile, a conjugated diene polymer having a small rolling resistance, good abrasion resistance and tensile properties, and vehicle stability which is represented by wet skid resistance is required as a rubber material for a tire.

In order to decrease the rolling resistance of the tire, a method of decreasing the hysteresis loss of vulcanized rubber is suggested. As the evaluation index of the vulcanized rubber, repulsive elasticity at 50° C. to 80° C., tan δ, Goodrich heating, etc. are used. That is, a rubber material having large repulsive elasticity or small tan δ or Goodrich heating is preferably used.

As a rubber material having small hysteresis loss, natural rubber, polyisoprene rubber, polybutadiene rubber, etc., are known, however these materials have small wet skid resistance. Recently, a conjugated diene (co)polymer such as styrene-butadiene rubber (hereinafter, will be referred to as SBR) and butadiene rubber (hereinafter, will be referred to as BR) is prepared by an emulsion polymerization or a solution polymerization, and used as rubber for a tire. The strongest points of the solution polymerization with respect to the emulsion polymerization includes that the amount of a vinyl structure and the amount of styrene regulating the physical properties of the rubber may be optionally controlled, and the molecular weight and the physical properties may be controlled via coupling, modification, etc. Therefore, the structure of the SBR or BR rubber finally produced may be easily change, the movement of the terminal of a chain may decrease due to the bonding or modification of the terminal of a chain, and the bonding force with a filler such as silica and carbon black may increase. Accordingly, the SBR rubber by the solution polymerization may be widely used as a rubber material for a tire.

In the case that such SBR obtained by the solution polymerization is used as the rubber material for a tire, the vinyl content in the SBR may increase, the glass transition temperature of the rubber may increase, physical properties required for the tire such as running resistance and breaking power may be controlled, and the glass transition temperature may be appropriately controlled, thereby reducing fuel consumption.

The SBR by the solution polymerization is prepared using an anion polymerization initiator, and is used after combining or modifying the terminal of the chain of the polymer thus formed using various modifiers.

Meanwhile, carbon black, silica, etc. are used as a filler for reinforcing a tire tread. In the case that the silica is used as the filler for reinforcing, low hysteresis loss and wet skid resistance may be improved. However, the silica with a hydrophilic surface with respect to carbon black with a hydrophobic surface has low affinity for rubber and inferior dispersibility, and a separate silane coupling agent is required to be used to improve dispersibility or impart bonding force between silica-rubber.

Accordingly, a method of introducing a functional group having affinity for or reactivity with silica at the terminal part of a rubber molecule is suggested, however effects thereof are insufficient.

In addition, in the case that the affinity only for the silica is increased, the affinity for the carbon black may be relatively deteriorated, and the application range thereof may be limited.

Accordingly, the development of rubber having high affinity for carbon black as well as silica is necessary.

DISCLOSURE OF THE INVENTION

Technical Problem

According to an aspect of the present invention to solve the limitations of the conventional technique, a modified styrene-butadiene copolymer having a high modification ratio is provided.

According to another aspect of the present invention, a method of preparing the modified styrene-butadiene copolymer is provided.

According to further another aspect of the present invention, a rubber composition including the modified styrene-butadiene copolymer is provided.

Also, according to another aspect of the present invention, a tire manufactured using the rubber composition is provided.

Further, according to another aspect of the present invention, a useful modifier for preparing the modified styrene-butadiene copolymer is provided.

Technical Solution

According to an aspect of the present invention, there is provided a modified styrene-butadiene copolymer including a functional group derived from a modifier represented by the following Formula 1.

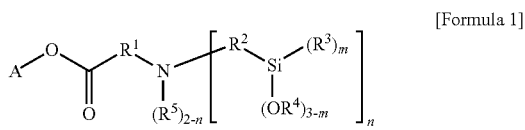

[Formula 1]

In the above Formula 1,
A is hydrocarbon of 1 to 20 carbon atoms, or hydrocarbon of 1 to 20 carbon atoms, including at least one heteroatom selected from the group consisting of N, S and O, $R^1$ and $R^2$ are each independently substituted or unsubstituted divalent hydrocarbon of 1 to 20 carbon atoms, the substituted hydrocarbon being substituted with at least one substituent selected from the group consisting of linear or branched alkyl of 1 to 20 carbon atoms, cycloalkyl of 3 to 20 carbon atoms and aryl of 6 to 30 carbon atoms, $R^3$ to $R^5$ are each independently monovalent hydrocarbon having 1 to 20 carbon atoms, m is an integer from 0 to 3, and n is an integer of 1 or 2, wherein in a case where A in the hydrocarbon of 1 to 20 carbon atoms, n is an integer of 2.

In addition, there is provided in the present invention, a method of preparing the modified styrene-butadiene copolymer including preparing an active polymer combined with an alkali metal by polymerizing an aromatic vinyl monomer and a conjugated diene monomer in the presence of an organometallic compound in a hydrocarbon solvent (step 1); and reacting the active polymer with a modifier represented by Formula 1 (step 2).

In addition, there is provided in the present invention a rubber composition including the modified styrene-butadiene copolymer.

Also, there is provided in the present invention a tire manufactured using the rubber composition.

Further, there is provided in the present invention a modifier having a structure of the above Formula 1.

Advantageous Effects

The modified styrene-butadiene copolymer according to the present invention includes a functional group derived from a modifier represented by Formula 1, for example, a tertiary amine, and a group having affinity for silica or a group having affinity for hexane, and may have good affinity for a filler such as silica and exhibit a high modification ratio.

In addition, the modified styrene-butadiene copolymer according to the present invention may easily produce a modified styrene-butadiene copolymer having a high modification ratio by using a modifier represented by Formula 1 and having a high solubility.

In addition, since the rubber composition according to the present invention includes a modified styrene-butadiene copolymer having good affinity for a filler, processability may be good, and as a result, processed goods (for example, a tire) manufactured using the rubber composition may have good tensile strength, abrasion resistance and wet surface resistance.

Also, since the modifier represented by Formula 1 according to the present invention includes a carbonyl group having high reactivity at the terminal of an anion, pattern viscosity due to hydrolysis and condensation reaction may not be increased.

BRIEF DESCRIPTION OF DRAWINGS

The following drawing accompanied with the present disclosure is for illustrating preferred embodiments of the present invention and plays the role of further understanding of the technical spirit of the present invention together with the features described above. Therefore, the present invention should not be limited and interpreted to the following description taken in conjunction with the accompanying drawings, in which:

FIG. 1 schematically illustrates a modification reaction using a modifier according to an embodiment of the present invention.

BEST MODE FOR CARRYING OUT THE INVENTION

Hereinafter, the present invention will be described in more detail to assist the understanding of the present invention.

It will be understood that words or terms used in the description and claims shall not be interpreted as the meaning used in common or defined in dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

The present invention provides a modified styrene-butadiene copolymer having good affinity for a filler and improved processability.

The modified styrene-butadiene copolymer according to an embodiment of the present invention includes a functional group derived from a modifier represented by the following Formula 1.

[Formula 1]

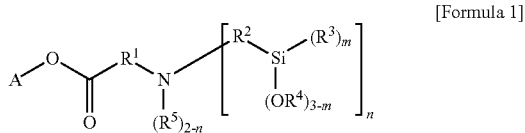

In the above Formula 1,

A is hydrocarbon of 1 to 20 carbon atoms, or hydrocarbon of 1 to 20 carbon atoms, including at least one heteroatom selected from the group consisting of N, S and O, $R^1$ and $R^2$ are each independently substituted or unsubstituted divalent hydrocarbon of 1 to 20 carbon atoms, the substituted hydrocarbon being substituted with at least one substituent selected from the group consisting of linear or branched alkyl of 1 to 20 carbon atoms, cycloalkyl of 3 to 20 carbon atoms and aryl of 6 to 30 carbon atoms, $R^3$ to $R^5$ are each independently monovalent hydrocarbon having 1 to 20 carbon atoms, and m is an integer from 0 to 3, and n is an integer of 1 or 2, wherein in a case where A in the hydrocarbon of 1 to 20 carbon atoms, n is an integer of 2.

The modified styrene-butadiene copolymer may be prepared by reacting an active polymer combined with an organo alkali metal with the modifier represented by the above Formula 1 via the following preparation method. The physical properties of the modified styrene-butadiene copolymer may be improved by including the functional group derived from the modifier represented by the above Formula 1.

The modifier represented by Formula 1 may include at least one of a functional group for improving the dispersibility of an inorganic filler, a functional group having affinity for an inorganic filler or a functional group having affinity for a solvent, as a functional group capable of improving the physical properties of the copolymer.

In particular, the modifier of Formula 1 includes an ester group having high reactivity with respect to the active part of an active polymer and may modify the styrene-butadiene copolymer with a high modification ratio. As a result, a substituted functional group in the modifier may be introduced into the styrene-butadiene copolymer with high yield. In addition, the modifier may be a functional group improving the dispersibility of the inorganic filler by preventing the cohesion between inorganic fillers in a rubber composition and may particularly include an amino group, particularly, a tertiary amino group. For example, in the case that silica is used as the inorganic filler, cohesion may be easily generated due to a hydrogen bonding between hydroxyl groups present on the surface thereof. The tertiary amino group in the modifier may prevent the hydrogen bond between hydroxyl groups to improve the dispersibility of silica. In addition, the modifier may include at least one of the functional group having affinity for the inorganic filler capable of improving the abrasion resistance and the processability of the rubber composition via interaction with the inorganic filler together with the amino group, or a functional group having affinity for a solvent having good affinity for a solvent used in the modification reaction of the styrene-butadiene copolymer. The functional group having affinity for the inorganic filler, particularly, an alkoxysilyl group may improve the abrasion resistance and the processability of the styrene-butadiene copolymer after being introduced to the styrene-butadiene copolymer and then being undergone a condensation reaction with the functional group at the surface of the inorganic filler, for example, in the case where the inorganic filler is silica, with a silanol group at the surface of the silica. Such an improving effect may increase with the increase of the number of the alkoxysilyl group. In addition, the functional group having affinity for the solvent may be a hydrocarbon group such as alkyl and aryl, which may increase the solubility of the modifier with respect to a solvent during conducting a modification process with respect to the styrene-butadiene copolymer. As a result, the modification ratio of the styrene-butadiene copolymer may increase.

In particular, in Formula 1, A may be hydrocarbon of 1 to 20 carbon atoms, or hydrocarbon of 1 to 20 carbon atoms, including at least one heteroatom selected from the group consisting of N, S and O.

In addition, in the case that A is hydrocarbon of 1 to 20 carbon atoms, A may be selected from the group consisting of alkyl of 1 to 20 carbon atoms, cycloalkyl of 3 to 20 carbon atoms, aryl of 6 to 20 carbon atoms, and arylalkyl of 7 to 20 carbon atoms. More particularly, A may be selected from the group consisting of alkyl of 1 to 10 carbon atoms, cycloalkyl of 3 to 12 carbon atoms, aryl of 6 to 12 carbon atoms, and arylalkyl of 7 to 12 carbon atoms.

In addition, in the case that A is hydrocarbon of 1 to 20 carbon atoms, including the heteroatom, A may be one in which a heteroatom is included instead of at least one carbon atom in the hydrocarbon; or one in which at least one hydrogen atom combined with a carbon atom in the hydrocarbon may be substituted with a heteroatom or a functional group including a heteroatom. In this case, the heteroatom may be selected from the group consisting of N, O and S. More particularly, in the case that A is hydrocarbon of 1 to 20 carbon atoms including a heteroatom, A may be alkoxy; phenoxy; carboxyl; acid anhydride; amino; amide; epoxy; mercapto; $-[R^{11}O]_xR^{12}$ (where $R^{11}$ is alkylene of 2 to 20 carbon atoms, $R^{12}$ is selected from the group consisting of a hydrogen atom, alkyl of 1 to 20 carbon atoms, cycloalkyl of 3 to 20 carbon atoms, aryl of 6 to 20 carbon atoms, and arylalkyl of 7 to 20 carbon atoms, and x is an integer from 2 to 10); hydrocarbon of 1 to 20 carbon atoms including at least one functional group selected from the group consisting of hydroxyl, alkoxy, phenoxy, carboxyl, ester, acid anhydride, amino, amide, epoxy and mercapto (for example, hydroxyalkyl, alkoxyalkyl, phenoxyalkyl, aminoalkyl or thiolalkyl). More particularly, in the case that A is alkyl of 1 to 20 carbon atoms, including a heteroatom, A may be selected from the group consisting of alkoxy of 1 to 20 carbon atoms, alkoxyalkyl of 2 to 20 carbon atoms, phenoxyalkyl of 7 to 20 carbon atoms, aminoalkyl of 1 to 20 carbon atoms and $-[R^{11}O]_xR^{12}$ (where $R^{11}$ is alkylene of 2 to 20 carbon atoms, $R^{12}$ is selected from the group consisting of a hydrogen atom, alkyl of 1 to 10 carbon atoms, cycloalkyl of 3 to 12 carbon atoms, aryl of 6 to 18 carbon atoms, and arylalkyl of 7 to 18 carbon atoms, and x is an integer of 2 to 10).

In addition, in Formula 1, $R^1$ and $R^2$ are each independently divalent hydrocarbon of 1 to 20 carbon atoms, and may be particularly, alkylene of 1 to 10 carbon atoms such as methylene, ethylene and propylene; arylene of 6 to 20 carbon atoms such as phenylene; or arylalkylene of 7 to 20 carbon atoms as the combination thereof. More particularly, $R^1$ and $R^2$ are each independently alkylene of 1 to 5 carbon atoms. Further particularly, $R^1$ may be alkylene of 2 or 3 carbon atoms, and $R^2$ may be alkylene of 1 to 3 carbon atoms. In addition, $R^1$ and $R^2$ may be each independently substituted with at least one substituent selected from the group consisting of linear or branched alkyl of 1 to 20 carbon atoms, cycloalkyl of 3 to 20 carbon atoms and aryl of 6 to 30 carbon atoms.

In addition, in Formula 1, $R^3$ to $R^5$ may be each independently monovalent hydrocarbon of 1 to 20 carbon atoms, and may particularly be selected from the group consisting of alkyl of 1 to 10 carbon atoms, cycloalkyl of 3 to 18 carbon atoms, aryl of 6 to 18 carbon atoms and the combination thereof. More particularly, $R^3$ and $R^4$ may be each independently alkyl of 1 to 5 carbon atoms, $R^5$ may be alkyl of 1 to 5 carbon atoms or cycloalkyl of 3 to 8 carbon atoms. More particularly, $R^3$ to $R^5$ may be each independently alkyl of 1 to 5 carbon atoms.

In addition, in Formula 1, m may be an integer from 0 to 3, and more particularly, an integer from 0 to 2. In addition, n may be an integer of 1 to 2, where A is hydrocarbon of 1 to 20 carbon atoms, n is an integer of 2.

More particularly, in the modifier in Formula 1, A may be one selected from the group consisting of alkyl of 1 to 10 carbon atoms, cycloalkyl of 3 to 12 carbon atoms, aryl of 6 to 12 carbon atoms, arylalkyl of 7 to 12 carbon atoms, alkoxyalkyl of 2 to 10 carbon atoms, phenoxyalkyl of 7 to 12 carbon atoms, aminoalkyl of 1 to 10 carbon atoms and $-[R^{11}O]_xR^{12}$ (where $R^{11}$ is alkylene of 2 to 10 carbon atoms, $R^{12}$ is selected from the group consisting of a hydrogen atom, alkyl of 1 to 10 carbon atoms, cycloalkyl of 3 to 12 carbon atoms, aryl of 6 to 18 carbon atoms, and arylalkyl of 7 to 18 carbon atoms, and x is an integer of 2 to 10). $R^1$ and $R^2$ are each independently alkylene of 1 or 5 carbon atoms, $R^3$ and $R^4$ are each independently alkyl of 1 to 5 carbon atoms, $R^5$ is alkyl of 1 to 5 carbon atoms or cycloalkyl of 3 to 8 carbon atoms, m is an integer of 0 to 2, and n is an integer of 1 or 2, where A is alkyl of 1 to 20 carbon atoms, cycloalkyl of 3 to 20 carbon atoms, aryl of 6 to 20 carbon atoms, or arylalkyl of 7 to 20 carbon atoms, n is an integer of 2.

More particularly, the modifier may be 2-methoxyethyl 3-(bis(3-triethoxysilylpropyl)amino)propanoate, 2-phenoxyethyl 3-(bis(3-(triethoxysilyl)propyl)amino)propanoate, 2-methoxyethyl 3-(bis(3-(diethoxy(methyl)silyl)propyl)

amino)propanoate, 2-ethoxyethyl 3-(bis(3-(diethoxy (methyl)silyl)propyl)amino)propanoate, ethyl 3-(bis(3-(diethoxy(methyl)silyl)propyl)amino)propanoate, 2-phenoxyethyl 3-(cyclohexyl((triethoxysilyl)methyl) amino)propanoate, 2-methoxyethyl 3-(cyclohexyl((triethoxysilyl)methyl)amino)propanoate, 2-dimethylaminoethyl 3-(cyclohexyl((triethoxysilyl)methyl)amino)propanoate, 2,5,8,11,14,17,20,23,26-nonaoxaoctacosan-28-yl 3-(bis(3-(triethoxysilyl)propyl)amino)propanoate, 2-(2-(2-(2-phenoxyethoxy)ethoxy)ethyl 3-(bis(3-(triethoxysilyl) propyl)amino)propanoate, 2-(dimethylamino)ethyl 3-(bis(3-(triethoxysilyl)propyl)amino)propanoate, 2-(2-(2-(2-phenoxyethoxy) ethoxy) ethoxy)ethyl 3-(cyclohexyl ((triethoxysilyl)methyl)amino)propanoate, 2-methoxyethyl 3-(bis(3-(diethoxy(methyl)silyl)propyl)amino)propanoate, or ethyl 3-(bis(3-(diethoxy(methyl)silyl)propyl)amino)propanoate. Among the compounds, one or a mixture of at least two may be used.

Among the compounds, the modifier of Formula 1 may be at least one selected from the group consisting of 2-phenoxyethyl 3-(cyclohexyl((triethoxysilyl)methyl)amino)propanoate, 2-methoxyethyl 3-(cyclohexyl((triethoxysilyl) methyl)amino)propanoate, 2-(dimethylamino)ethyl 3-(cyclohexyl((triethoxysilyl)methyl)amino)propanoate, 2,5,8,11,14,17,20,23,26-nonaoxaoctacosane-28-yl 3-(bis(3-(triethoxysilyl)propyl)amino)propanoate, 2-(2-(2-(2-phenoxyethoxy)ethoxy)ethyl 3-(bis(3-(triethoxysilyl) propyl)amino)propanoate, 2-phenoxyethyl 3-(bis(3-triethoxysilyl)propyl)amino)propanoate, 2-methoxyethyl 3-(bis(3-(triethoxysilyl)propyl)amino)propanoate, 2-(dimethylamino)ethyl 3-(bis(3-triethoxysilyl)propyl)amino)propanoate, 2-(2-(2-(2-phenoxyethoxy)ethoxy)ethoxy)ethyl 3-(cyclohexyl((triethoxysilyl)methyl)amino)propanoate, 2-methoxyethyl 3-(bis(3-(diethoxy(methyl)silyl)propyl) amino)propanoate, and ethyl 3-(bis(3-(diethoxy(methyl)silyl)propyl)amino)propanoate.

In addition, the modifier may have solubility of 10 g or more with respect to 100 g of a non-polar solvent such as hexane at 25° C. under 1 atm. Here, the solubility of the modifier means the degree of clear dissolution without turbidity when observed with naked eyes. With such high solubility, a good modification ratio with respect to the styrene-butadiene copolymer may be attained.

The modifier according to the present invention has an optimized functional group which may maximize affinity for an inorganic filler and a solvent, and used as the modifier of the styrene-butadiene copolymer to impart the styrene-butadiene copolymer with good viscoelasticity, tensile properties, and processability.

Meanwhile, the modified styrene-butadiene copolymer may be a copolymer of a conjugated diene monomer and an aromatic vinyl monomer. That is, the modified styrene-butadiene copolymer may include a conjugated diene monomer derived unit and an aromatic vinyl monomer derived unit.

In the present invention, the terms "derived unit" may mean a component or a structure come from a material, or the material itself.

In addition, the modified styrene-butadiene copolymer may be a random copolymer.

In the present invention, the terms "random copolymer" may mean random arrangement of constituting units composing a copolymer.

The conjugated diene monomer is not specifically limited, however may be at least one selected from the group consisting of 1,3-butadiene, 2,3-dimethyl-1,3-butadiene, piperylene, 3-butyl-1,3-octadiene, isoprene and 2-phenyl-1, 3-butadiene.

The modified styrene-butadiene copolymer may include 60 wt % or more, particularly, from 60 wt % to 90 wt %, and more particularly, from 60 wt % to 85 wt % of the conjugated diene monomer derived unit.

The aromatic vinyl monomer is not specifically limited, however may be at least one selected from the group consisting of styrene, α-methyl styrene, 3-methyl styrene, 4-methyl styrene, 4-propyl styrene, 1-vinylnaphthalene, 4-cyclohexylstyrene, 4-(p-methylphenyl)styrene and 1-vinyl-5-hexylnaphthalene.

The modified styrene-butadiene copolymer may include an aromatic vinyl monomer derived unit in an amount ratio of 40 wt % or less, particularly, from 10 wt % to 40 wt %, and more particularly, from 15 wt % to 40 wt %.

In addition, the modified styrene-butadiene copolymer may have a number average molecular weight of 1,000 g/mol to 2,000,000 g/mol, particularly, from 10,000 g/mol to 2,000,000 g/mol, and more particularly, from 100,000 g/mol to 2,000,000 g/mol.

The modified styrene-butadiene copolymer may have a molecular weight distribution (Mw/Mn) of 1.1 to 10, particularly, 1.1 to 5, and more particularly, 1.1 to 4. In the case that the modified styrene-butadiene copolymer has the above-described molecular weight distribution, a rubber composition including the same may have improved processability, and as a result, the mechanical properties, the low fuel consumption properties and the abrasion resistance of a molded product thus manufactured may be improved.

In addition, the modified styrene-butadiene copolymer may have a vinyl content of 5 wt %, particularly, 10 wt % or more, and more particularly, from 14 wt % to 70 wt %. In the case that the modified styrene-butadiene copolymer has the vinyl content in the above range, a glass transition temperature may be controlled to an appropriate range, and in the case of applying thereof to a tire, physical properties required for a tire such as running resistance and breaking force may be satisfied, and fuel consumption may be decreased.

Here, the vinyl content means the amount of not 1,4-added but 1,2-added conjugated diene monomer on the basis of 100 wt % of the styrene-butadiene copolymer composed of a monomer having a vinyl group and an aromatic vinyl monomer.

In addition, there is provided in the present invention a method of preparing a modified styrene-butadiene copolymer including a group derived from a modifier represented by Formula 1.

The preparation method according to an embodiment of the present invention is characterized in including a step of preparing an active polymer combined with an alkali metal by polymerizing an aromatic vinyl monomer and a conjugated diene monomer in the presence of an organometallic compound in a hydrocarbon solvent (step 1); and a step of reacting the active polymer with a modifier represented by the following Formula 1 (step 2).

[Formula 1]

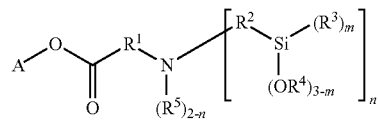

In the above Formula 1,

A is hydrocarbon of 1 to 20 carbon atoms, or hydrocarbon of 1 to 20 carbon atoms, including at least one heteroatom selected from the group consisting of N, S and O, $R^1$ and $R^2$ are each independently substituted or unsubstituted divalent hydrocarbon of 1 to 20 carbon atoms, the substituted hydrocarbon being substituted with at least one substituent selected from the group consisting of linear or branched alkyl of 1 to 20 carbon atoms, cycloalkyl of 3 to 20 carbon atoms and aryl of 6 to 30 carbon atoms, $R^3$ to $R^5$ are each independently monovalent hydrocarbon having 1 to 20 carbon atoms, m is an integer from 0 to 3, and n is an integer of 1 or 2, wherein in a case where A in the hydrocarbon of 1 to 20 carbon atoms, n is an integer of 2.

Step 1 is a step for preparing an active polymer combined with an organic metal and may be performed by polymerizing a conjugated diene monomer and an aromatic vinyl monomer in the presence of an organometallic compound in a hydrocarbon solvent.

The active polymer may represent a polymer in which a polymer anion and an organometallic cation are combined.

Particular kinds of the conjugated diene monomer and the aromatic vinyl monomer may be the same as described above, and the amount used of each monomer may be appropriately controlled so that the amounts of the conjugated diene monomer derived unit and the aromatic vinyl monomer derived unit in the modified styrene-butadiene copolymer are in the range described above.

The hydrocarbon solvent is not specifically limited, however may be at least one selected from the group consisting of n-pentane, n-hexane, n-heptane, isooctane, cyclohexane, toluene, benzene and xylene.

The organometallic compound may be at least one selected from the group consisting of an organo alkali metal compound, an organolithium compound, an organosodium compound, an organopotassium compound, an organorubidium compound and an organocesium compound.

In particular, the organometallic compound may be at least one selected from the group consisting of methyllithium, ethyllithium, propyllithium, n-butyllithium, s-butyllithium, t-butyllithium, hexyllithium, n-decyllithium, t-octyllithium, phenyllithium, 1-naphthyllithium, n-eicosyllithium, 4-butylphenyllithium, 4-tolyllithium, cyclohexyllithium, 3,5-di-n-heptylcyclohexyllithium, 4-cyclopentyllithium, naphthyllithium, naphthylsodium, naphthylpotassium, lithium alkoxide, sodium alkoxide, potassium alkoxide, lithium sulfonate, sodium sulfonate, potassium sulfonate, lithium amide, sodium amide, potassium amide, and lithium isopropyl amide.

The organometallic compound may be used in an amount of 0.01 mmol to 10 mmol on the basis of 100 g of the total monomer. Particularly, the organometallic compound may be used in an amount of 0.05 mmol to 5 mmol, particularly, 0.1 mmol to 2 mmol, and more particularly, 0.1 mmol to 1 mmol on the basis of 100 g of the total monomer.

The polymerization in step 1 may be performed after further adding a polar additive as occasion demands, and the amount of the polar additive may be from 0.001 g to 50 g, particularly, from 0.001 g to 10 g, and more particularly, from 0.005 g to 0.1 g on the basis of 100 g of the total monomer.

In addition, the amount of the polar additive may be from 0.001 g to 10 g, particularly, from 0.005 g to 1 g, and more particularly, from 0.005 g to 0.1 g on the basis of 1 mmol of the total amount of the organometallic compound.

The polar additive may be at least one selected from the group consisting of salts, ethers, amines, or a mixture thereof, and particularly, tetrahydrofuran, ditetrahydrofurylpropane, diethyl ether, cycloamyl ether, dipropyl ether, ethylenedimethyl ether, ethylenedimethyl ether, diethylene glycol, dimethyl ether, tertiary butoxyethoxyethane bis(3-dimethylaminoethyl) ether, (dimethylaminoethyl)ethyl ether, trimethylamine, triethylamine, tripropylamine, and tetramethylethylenediamine. More particularly, ditetrahydropropylpropane, triethylamine or tetramethylethylenediamine may be used.

In the preparation method according to an embodiment of the present invention, in the case that the conjugated diene monomer and the aromatic vinyl monomer are copolymerized using the polar additive, the difference of the reaction rates thereof may be compensated to produce a random copolymer easily.

The polymerization in step 1 may be an anionic polymerization and may particularly be a living anionic polymerization by which an active part may be obtained via a growth reaction by anions.

In addition, the polymerization may be a heating polymerization, an isothermal polymerization, or a constant temperature polymerization (insulation polymerization).

Here, the constant temperature polymerization is a polymerization method including a step of polymerizing without applying heat optionally but using heat from the reaction itself after injecting an organometallic compound. The heating polymerization is a polymerization method by which heat is applied optionally to increase the temperature after injecting an organometallic compound. The isothermal polymerization is a polymerization method by which the temperature of a polymer is maintained constant by applying or taking heat after injecting the organometallic compound.

The polymerization may be performed in a temperature range of −20° C. to 200° C., particularly, from 0° C. to 150° C., and more particularly, from 10° C. to 120° C.

Step 2 is a step of reacting the active polymer and the modifier represented by Formula 1 to prepare the modified styrene-butadiene copolymer.

The modifier represented by Formula 1 may be the same as described above, and one or a mixture of at least two materials may be used in the reaction.

The modifier represented by Formula 1 may be used in an amount of 0.1 mol to 10 mol relative to 1 mol of the organometallic compound. Particularly, the modifier represented by Formula 1 may be used in an amount of 0.3 mol to 2 mol relative to 1 mol of the organometallic compound. In the case that the modifier is used in an amount satisfying the ratio range, a modification reaction with optimized performance may be attained, and a styrene-butadiene copolymer with a high modification ratio may be obtained.

The reaction of step 2 is a modification reaction for introducing a functional group to a copolymer and may be performed at 0° C. to 90° C. for from 1 minute to 5 hours.

In addition, the preparation method of the modified styrene-butadiene copolymer according to an embodiment of the present invention may be performed by a batch type polymerization method or a continuous type polymerization method including at least one reactor.

The preparation method according to an embodiment of the present invention may further include at least one step of recovering or drying of solvents or unreacted monomers after step 2 as occasion demands.

In addition, there is provided in the present invention a rubber composition including the modified styrene-butadiene copolymer.

The rubber composition according to an embodiment of the present invention may include 10 wt % or more, particularly, from 10 wt % to 100 wt %, and more particularly, from 20 wt % to 90 wt % of the modified styrene-butadiene copolymer. In the case that the amount of the modified styrene-butadiene copolymer is less than 10 wt %, the improving effect of the abrasion resistance and the crack resistance of a product manufactured using the rubber composition, for example, a tire, may be insignificant.

In addition, the rubber composition may further include other rubber components as well as the modified styrene-butadiene copolymer as occasion demands. In this case, the rubber component may be included in an amount ratio of 90 wt % or less relative to the total amount of the rubber composition. In particular, the rubber component may be included in an amount ratio of 1 to 900 parts by weight relative to 100 parts by weight of the modified styrene-butadiene copolymer.

The rubber component may be natural rubber or synthetic rubber, for example, the rubber component may include natural rubber (NR) including cis-1,4-polyisoprene; modified natural rubber such as epoxidized natural rubber (ENR), deproteinized natural rubber (DPNR), and hydrogenated natural rubber, which are obtained by modifying or purifying common natural rubber; or synthetic rubber such as styrene-butadiene copolymer (SBR), polybutadiene (BR), polyisoprene (IR), butyl rubber (IIR), ethylene-propylene copolymer, polyisobutylene-co-isoprene, neoprene, poly(ethylene-co-propylene), poly(styrene-co-butadiene), poly(styrene-co-isoprene), poly(styrene-co-isoprene-co-butadiene), poly(isoprene-co-butadiene), poly(ethylene-co-propylene-co-diene), polysulfide rubber, acryl rubber, urethane rubber, silicone rubber, epichlorohydrin rubber, butyl rubber, and halogenated butyl rubber, and one or a mixture of at least two thereof may be used.

In addition, the rubber composition may include 0.1 to 200 parts by weight of a filler, particularly, 10 to 120 parts by weight of a filler relative to 100 parts by weight of a modified styrene-butadiene copolymer.

The filler may be a silica filler, and the silica filler is not specifically limited and may include, for example, wet silica (hydrous silicate), dry silica (anhydrous silicate), calcium silicate, aluminum silicate or colloidal silica. More particularly, the filler may be the wet silica having the most remarkable effects of the improving effect of breaking properties and the compatible effect of wet grip.

In addition, the rubber composition according to an embodiment of the present invention may further include a carbon black filler as occasion demands.

Meanwhile, in the case that silica is used as the filler, a silane coupling agent may be used together to improve reinforcing properties and low heating properties.

The silane coupling agent may particularly include bis(3-triethoxysilylpropyl)tetrasulfide, bis(3-triethoxysilylpropyl)trisulfide, bis(3-triethoxysilylpropyl)disulfide, bis(2-triethoxysilylethyl)tetrasulfide, bis(3-trimethoxysilylpropyl)tetrasulfide, bis(2-trimethoxysilylethyl)tetrasulfide, 3-mercaptopropyltrimethoxysilane, 3-mercaptopropyltriethoxysilane, 2-mercaptoethyltrimethoxysilane, 2-mercaptoethyltriethoxysilane, 3-trimethoxysilylpropyl-N,N-dimethylthiocarbamoyltetrasulfide, 3-triethoxysilylpropyl-N,N-dimethylthiocarbamoyltetrasulfide, 2-triethoxysilylethyl-N,N-dimethylthiocarbamoyltetrasulfide, 3-trimethoxysilylpropylbenzothiazolyltetrasulfide, 3-triethoxysilylpropylbenzolyltetrasulfide, 3-triethoxysilylpropylmethacrylatemonosulfide, 3-trimethoxysilylpropylmethacrylatemonosulfide, bis(3-diethoxymethylsilylpropyl)tetrasulfide, 3-mercaptopropyldimethoxymethylsilane, dimethoxymethylsilylpropyl-N,N-dimethylthiocarbamoyltetrasulfide, or dimethoxymethylsilylpropylbenzothiazolyltetrasulfide, and one or a mixture of at least two thereof may be used. More particularly, the silane coupling agent may be bis(3-triethoxysilylpropyl)polysulfide or 3-trimethoxysilylpropylbenzothiazyltetrasulfide in consideration of the improving effect of reinforcing properties.

In addition, the rubber composition according to an embodiment of the present invention may be sulfur cross-linkable, and so may further include a vulcanizing agent.

The vulcanizing agent may be particularly a sulfur powder and may be included in an amount ratio of 0.1 to 10 parts by weight relative to 100 parts by weight of a rubber component. In the case that the vulcanizing agent is included in the above amount range, the elasticity and the strength required for the vulcanized rubber composition may be secured, and at the same time, a low combustion ratio may be attained.

In addition, the rubber composition according to an embodiment of the present invention may further include various additives used in common rubber industry other than the above components, particularly, a vulcanization accelerator, a process oil, a plasticizer, an antiaging agent, a scorch preventing agent, a zinc white, stearic acid, a thermosetting resin, or a thermoplastic resin.

The vulcanization accelerator is not specifically limited and particularly includes a thiazole compound such as 2-mercaptobenzothiazole (M), dibenzothiazyldisulfide (DM), N-cyclohexyl-2-benzothiazylsulfenamide (CZ), etc. or a guanidine compound such as diphenylguanidine (DPG). The vulcanization accelerator may be included in an amount ratio of 0.1 to 5 parts by weight relative to 100 parts by weight of the rubber component.

In addition, the process oil plays the role of a softener in a rubber composition and may particularly include paraffins, naphthenes, or aromatic compounds. More particularly, an aromatic process oil may be used in consideration of tensile strength and abrasion resistance, and the naphthene or paraffin process oil may be used in consideration of hysteresis loss and low temperature properties. The process oil may be included in an amount ratio of 100 parts by weight or less relative to 100 parts by weight of the rubber component. In the case of using the above-described amount, the deterioration of the tensile strength and the low heating properties (a low fuel combustion ratio) of the vulcanized rubber may be prevented.

In addition, the antiaging agent may particularly include N-isopropyl-N'-phenyl-p-phenylenediamine, N-(1,3-dimethylbutyl)-N'-phenyl-p-phenylenediamine, 6-ethoxy-2,2,4-trimethyl-1,2-dihydroquinoline, or a condensate of diphenylamine and acetone at a high temperature. The antiaging agent may be used in an amount ratio of 0.1 to 6 parts by weight relative to 100 parts by weight of the rubber component.

The rubber composition according to an embodiment of the present invention may be obtained by mulling using a mulling apparatus such as a banbury mixer, a roll, and an internal mixer according to the mixing prescription. After a molding process, a rubber composition having low heating properties and good abrasion resistance may be obtained by the vulcanizing process.

Therefore, the rubber composition may be usefully used for the manufacture of the members of a tire such as a tire tread, an under tread, a side wall, a carcass coating rubber, a belt coating rubber, a bead filler, a chafer, and a bead coating rubber, or for the manufacture of a rubber product for various industries such as a dustproof rubber, a belt conveyor, and a hose.

Also, there is provided in the present invention a tire manufactured using the rubber composition. The tire may include a tire or a tire tread.

Further, there is provided in the present invention a modifier useful for the modification of the modified styrene-butadiene copolymer.

The modifier is the same as described above.

Meanwhile, the modifier represented by Formula 1 according to an embodiment of the present invention may be prepared by the reaction of a compound of the following Formula 2 and a compound of the following Formula 3.

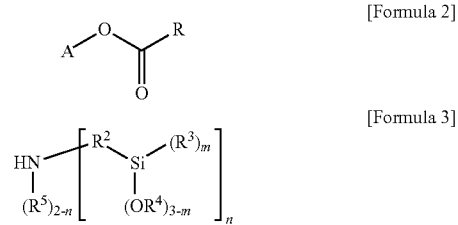

In Formulae 2 and 3, A, $R^2$ to $R^5$, m and n are the same as explained above, R may be alkenyl of 2 to 20 carbon atoms substituted with at least one substituent selected from the group consisting of linear or branched alkyl of 1 to 20 carbon atoms, cycloalkyl of 3 to 20 carbon atoms and aryl of 6 to 30 carbon atoms, or unsubstituted alkenyl of 2 to 20 carbon atoms.

More particularly, in Formula 2, R may be alkenyl of 2 to 10 carbon atoms, and more particularly, alkenyl of 2 to 5 carbon atoms such as ethylene.

More particularly, the compound of Formula 2 may be ethylene glycol methyl ether acrylate, 2-phenoxyethyl acrylate, ethyl acrylate, etc. In addition, the compound of Formula 3 may be bis[3-(triethoxysilyl)propyl]amine, bis(m-ethyldiethoxysilylpropyl)amine, etc.

The compound of Formulae 2 and 3 may be used in stoichiometric amounts and particularly, 0.01 to 0.2 molar ratio, more particularly, 0.05 to 0.1 molar ratio, and further particularly, 0.05 to 0.08 molar ratio of the compound of Formula 3 may be used relative to 1 mol of the compound of Formula 2.

In addition, the reaction of the compound of Formula 2 and the compound of Formula 3 may be performed in an aqueous solvent. The aqueous solvent may particularly include an alcohol (for example, a lower alcohol of 1 to 5 carbon atoms such as ethanol), and one or a mixture of at least two thereof may be used.

In addition, the reaction of the compound of Formula 2 and the compound of Formula 3 may be performed under an inert gas atmosphere. In particular, the inert gas may include nitrogen, argon, etc.

In addition, the reaction of the compound of Formula 2 and the compound of Formula 3 may be conducted in a temperature range of 20° C. to 60° C. In the case that the temperature during the reaction is less than 20° C., a reaction rate may be too slow, and reaction efficiency may be deteriorated. In the case that the temperature during the reaction is greater than 60° C., the reaction rate may be too fast, the control of the reaction may be difficult, and side reaction may be generated.

According to the preparation method, a modifier including a functional group having affinity for a filler and a functional group having affinity for a solvent in a single molecule may be easily prepared.

Hereinafter, the present invention will be explained in more detail referring to embodiments and experimental embodiment. However, the following embodiments and experimental embodiments are for illustration, and the scope of the present invention is not limited thereto.

Preparation Example 1: Preparation of 2-phenoxyethyl 3-(cyclohexyl((triethoxysilyl)methyl)amino) propanoate To a 50 ml, round-bottomed flask, 5.744 mmol of (N-cyclohexylaminomethyl)triethoxysilane (Gelest Co.) and 5 ml of ethanol were added for dissolving, and 5.744 mmol of 2-phenoxyethyl acrylate (TCI Co.) was added thereto, followed by stirring at room temperature in nitrogen conditions for 8 hours. After finishing the reaction, solvents were removed under a reduced pressure and distilled at 120° C. under a reduced pressure to obtain 4.990 mmol of a 2-phenoxyethyl 3-(cyclohexyl((triethoxysilyl)methyl)amino)propanoate compound of Formula (i) (Yield 91.4%). $^1$H NMR spectroscopic data of separated 2-phenoxyethyl 3-(cyclohexyl((triethoxysilyl)methyl)amino)propanoate are as follows.

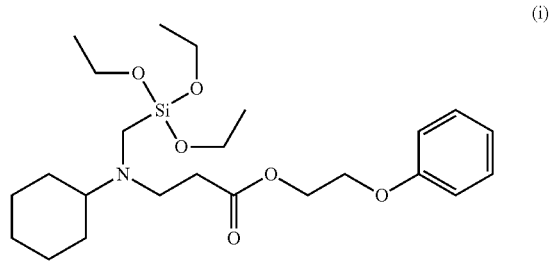 [SMILES: CCO[Si](CN(CCC(=O)OCCOc1ccccc1)C1CCCCC1)(OCC)OCC]

$^1$H-NMR (500 MHz, CDCl$_3$) δ 7.49-7.23 (m, 2H), δ 6.97-6.86 (m, 3H), δ 4.40-4.36 (m, 2H), δ 4.16-34.03 (m, 4H), δ 3.87-3.81 (m, 3H), δ 2.78-2.75 (m, 2H), δ 2.50-2.41 (m, 4H), δ 2.17-2.11 (m, 3H), δ 1.72-1.56 (m, 7H), δ 1.26-1.16 (m, 12H)

Preparation Example 2: Preparation of 2-methoxyethyl 3-(cyclohexyl((triethoxysilyl)methyl)amino) propanoate To a 50 ml, round-bottomed flask, 8.468 mmol of (N-cyclohexylaminomethyl)triethoxysilane (Gelest Co.) and 5 ml of ethanol were added for dissolving, and 8.468 mmol of ethylene glycol methyl ether acrylate (Acros Co.) was added thereto, followed by stirring at room temperature in nitrogen conditions for 8 hours. After finishing the reaction, solvents were removed under a reduced pressure and distilled at 120° C. under a reduced pressure to obtain 8.19 mmol of a 2-methoxyethyl 3-(cyclohexyl((triethoxysilyl)methyl) amino)propanoate compound of Formula (ii) (Yield 96.7%). $^1$H NMR spectroscopic data of separated 2-methoxyethyl 3-(cyclohexyl((triethoxysilyl)methyl)amino)propanoate are as follows.

(ii)

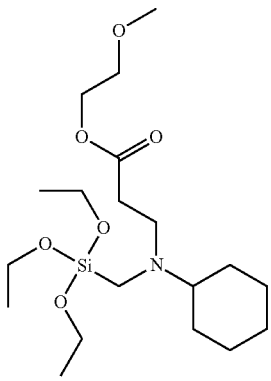

¹H-NMR (500 MHz, CDCl₃) δ 4.18-4.16 (t, 2H), δ 3.84-3.79 (m, 3H), δ3.55-3.54 (t, 2H), δ 3.35 (s, 3H), δ 2.76-2.73 (m, 2H), δ 2.48-2.45 (m, 4H), δ2.14-2.08 (m, 3H), δ 1.73-1.71 (m, 7H), δ 1.22-1.18 (m, 13H)

Preparation Example 3: Preparation of 2-(dimethylamino)ethyl 3-(cyclohexyl((triethoxysilyl)methyl)amino)propanoate To a 50 ml, round-bottomed flask, 6.586 mmol of (N-cyclohexylaminomethyl)triethoxysilane (Gelest Co.) and 5 ml of ethanol were added for dissolving, and 6.586 mmol of 2-(dimethylamino)ethyl acrylate (Sigma-Aldrich Co.) was added thereto, followed by stirring at room temperature in nitrogen conditions for 8 hours. After finishing the reaction, solvents were removed under a reduced pressure and distilled at 120° C. under a reduced pressure to obtain 6.24 mmol of a 2-(dimethylamino)ethyl 3-(cyclohexyl((triethoxysilyl)methyl)amino)propanoate compound of Formula (iii) (Yield 94.8%). ¹H NMR spectroscopic data of separated 2-(dimethylamino)ethyl 3-(cyclohexyl((triethoxysilyl)methyl)amino)propanoate are as follows.

(iii)

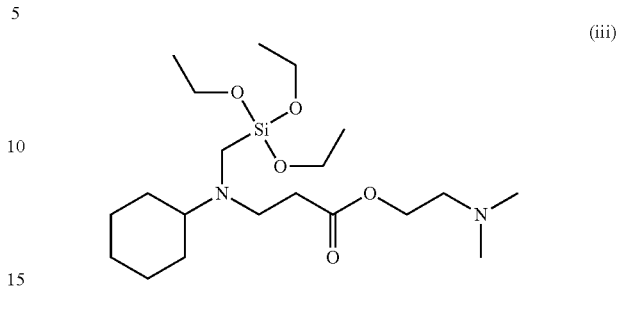

¹H-NMR (500 MHz, CDCl₃) δ 4.16-4.08 (m, 3H), δ 2.76-2.73 (m, 2H), δ2.53-2.50 (m, 3H), δ 2.47-2.41 (m, 3H), δ 2.25-2.23 (m, 10H), δ 2.11-2.08 (t, 2H), δ 1.73-1.72 (m, 9H), δ 1.54-1.47 (m, 4H), δ 1.24-1.16 (m, 10H)

Preparation Example 4: Preparation of 2,5,8,11,14,17,20,23,26-nonaoxaoctacosane-28-yl 3-(bis(3-(triethoxysilyl)propyl)amino)propanoate To a 50 ml, round-bottomed flask, 2.279 mmol of bis(3-triethoxysilylpropyl)amine (Gelest Co.) and 5 ml of ethanol were added for dissolving, and 2.279 mmol of poly(ethylene glycol) methyl ether acrylate (Sigma-Aldrich Co.) was added thereto, followed by stirring at room temperature in nitrogen conditions for 8 hours. After finishing the reaction, solvents were removed under a reduced pressure and distilled at 120° C. under a reduced pressure to obtain 2.13 mmol of a 2,5,8,11,14,17,20,23,26-nonaoxaoctacosane-28-yl 3-(bis(3-(triethoxysilyl)propyl)amino)propanoate compound of Formula (iv) (Yield 93.5%). ¹H NMR spectroscopic data of separated 2,5,8,11,14,17,20,23,26-nonaoxaoctacosane-28-yl 3-(bis(3-(triethoxysilyl)propyl)amino)propanoate are as follows.

(iv)

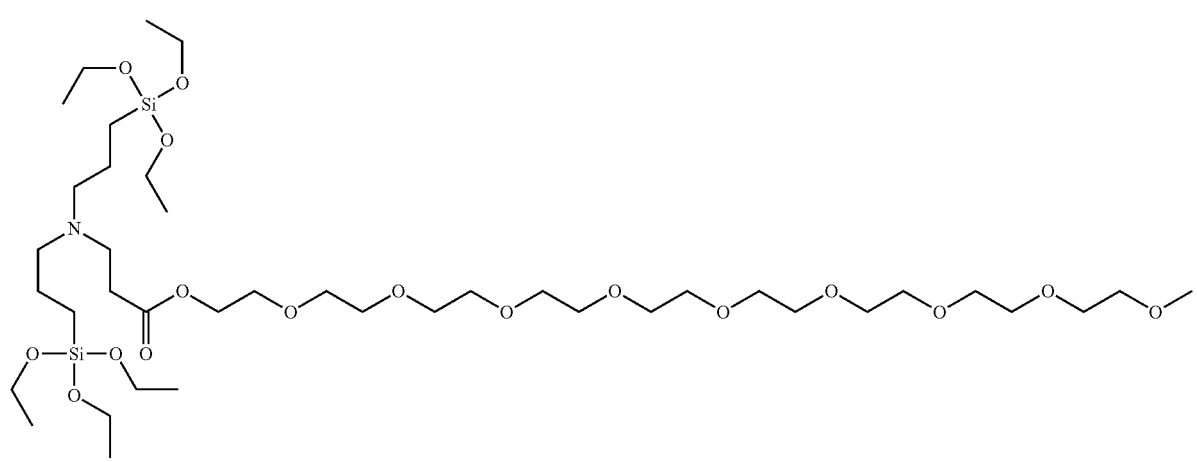

¹H-NMR (500 MHz, CDCl₃) δ 4.17-4.15 (t, 2H), δ 3.78-3.73 (m, 12H), δ 3.60-3.59 (m, 32H), δ 3.50-3.48 (m, 2H), δ 3.32 (s, 3H), δ 2.74-2.71 (m, 2H), δ 2.37-2.34 (t, 6H), δ 1.50-1.43 (m, 4H), δ 1.19-1.15 (t, 18H), δ 0.54-0.50 (m, 4H)

Preparation Example 5: Preparation of 2-(2-(2-(2-phenoxyethoxy)ethoxy)ethoxy)ethyl 3-(bis(3-triethoxysilyl)propyl)amino)propanoate To a 50 ml, round-bottomed flask, 2.279 mmol of bis(3-triethoxysilylpropyl)amine and 5 ml of ethanol were added for dissolving, and 2.279 mmol of poly(ethylene glycol) phenyl ether acrylate (Sigma-Aldrich, Mn 324) was added thereto, followed by stirring at room temperature in nitrogen conditions for 8 hours. After finishing the reaction, solvents were removed under a reduced pressure and distilled at 120° C. under a reduced pressure to obtain 2.15 mmol of a 2-(2-(2-(2-phenoxyethoy)ethoxy)ethoxy)ethyl 3-(bis(3-triethoxysilyl)propyl)amino)propanoate compound of Formula (v) (Yield 93.7%). ¹H NMR spectroscopic data of separated 2-(2-(2-(2-phenoxyethoy)ethoxy)ethoxy)ethyl 3-(bis(3-triethoxysilyl)propyl)amino)propanoate are as follows.

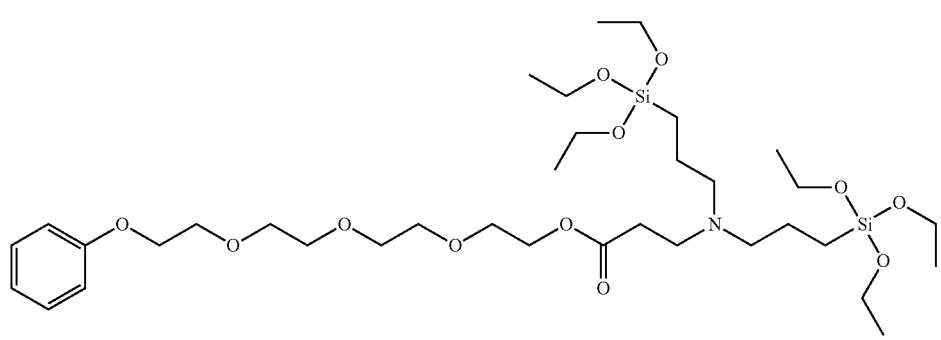

(v)

¹H-NMR (500 MHz, CDCl₃) δ 7.26-7.22 (t, 2H), δ 6.92-6.87 (m, 3H), δ4.20-4.17 (t, 2H), δ 4.11-4.07 (m, 3H), δ 3.84-3.82 (m, 2H), δ 3.81-3.75 (m, 10H), δ 3.71-3.60 (m, 10H), δ 2.77-2.74 (t, 2H), δ 2.39-2.36 (t, 6H), δ1.52-1.46 (m, 4H), δ 1.21-1.78 (m, 18H), δ 0.57-0.53 (m, 4H)

Preparation Example 6: Preparation of 2-phenoxyethyl 3-(bis(3-(triethoxysilyl)propyl)amino)propanoate To a 50 ml, round-bottomed flask, 4.557 mmol of bis(3-triethoxysilylpropyl)amine (Gelest Co.) and 5 ml of ethanol were added for dissolving, and 4.557 mmol of 2-phenoxyethyl acrylate (TCI Co.) was added thereto, followed by stirring at room temperature in nitrogen conditions for 8 hours. After finishing the reaction, solvents were removed under a reduced pressure and distilled at 120° C. under a reduced pressure to obtain 4.17 mmol of a 2-phenoxyethyl 3-(bis(3-(triethoxysilyl)propyl)amino)propanoate compound of Formula (vi) (Yield 91.6%). ¹H NMR spectroscopic data of separated 2-phenoxyethyl 3-(bis(3-(triethoxysilyl)propyl)amino)propanoate are as follows.

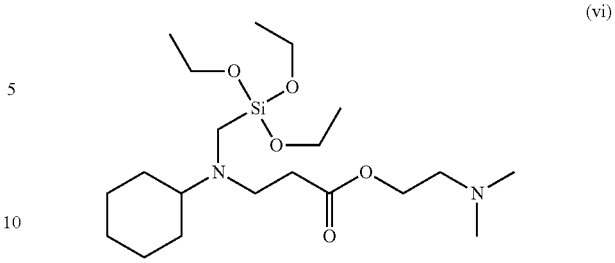

(vi)

¹H-NMR (500 MHz, CDCl₃) δ 7.26-7.23 (m, 2H), δ 6.94-6.84 (m, 3H), δ4.39-4.37 (t, 2H), δ 4.14-4.12 (t, 3H), δ 3.79-3.75 (m, 12H), δ 2.78-2.75 (t, 2H), δ 2.46-2.43 (t, 2H), δ 2.39-2.36 (t, 4H), δ 1.63-1.43 (m, 4H), δ 1.20-1.17 (m, 18H), δ 0.56-0.52 (m, 4H)

Preparation Example 7: Preparation of 2-methoxyethyl 3-(bis(3-(triethoxysilyl)propyl)amino)propanoate To a 50 ml, round-bottomed flask, 4.557 mmol of bis(3-triethoxysilylpropyl)amine (Gelest Co.) and 5 ml of ethanol were added for dissolving, and 4.557 mmol of ethylene glycol methyl ether acrylate (Acros Co.) was added thereto, followed by stirring at room temperature in nitrogen conditions for 8 hours. After finishing the reaction, solvents were removed under a reduced pressure and distilled at 120° C. under a reduced pressure to obtain 4.430 mmol of a 2-methoxyethyl 3-(bis(3-(triethoxysilyl)propyl)amino)propanoate compound of Formula (vii) (Yield 97.3%). ¹H NMR spectroscopic data of separated 2-methoxyethyl 3-(bis(3-triethoxysilyl)propyl)amino)propanoate are as follows.

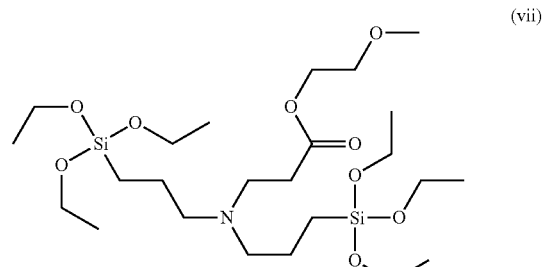

(vii)

¹H-NMR (500 MHz, CDCl₃) δ 4.21-4.19 (t, 2H), δ 3.81-3.77 (m, 12H), δ 3.57-3.56 (t, 2H), δ 3.36 (s, 3H), δ

2.79-2.76 (t, 2H), δ 2.47-2.44 (t, 2H), δ 2.40-2.37 (t, 4H), δ 1.54-1.47 (m, 4H), δ 1.22-1.19 (t, 18H), δ 0.57-0.54 (t, 4H)

Preparation Example 8: Preparation of 2-(dimethylamino)ethyl 3-(bis(3-triethoxysilyl)propyl)amino)propanoate To a 50 ml, round-bottomed flask, 4.5573 mmol of bis(3-triethoxysilylpropyl)amine (Gelest Co.) and 5 ml of ethanol were added for dissolving, and 4.55764 mmol of 2-(dimethylamino)ethyl acrylate (Sigma-Aldrich Co.) was added thereto, followed by stirring at room temperature in nitrogen conditions for 8 hours. After finishing the reaction, solvents were removed under a reduced pressure and distilled at 120° C. under a reduced pressure to obtain 4.18 mmol of a 2-(dimethylamino)ethyl 3-(bis(3-(triethoxysilyl)propyl)amino)propanoate compound of Formula (viii) (Yield 91.7%). ¹H NMR spectroscopic data of separated 2-(dimethylamino)ethyl 3-(bis(3-(triethoxysilyl)propyl)amino)propanoate are as follows.

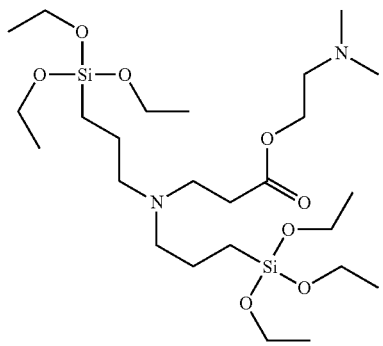

(viii)

¹H-NMR (500 MHz, CDCl₃) δ 4.12-4.09 (t, 2H), δ 3.78-3.74 (m, 12H), δ 2.75-2.73 (t, 2H), δ 2.51-2.49 (t, 3H), δ 2.42-2.40 (t, 2H), δ 2.37-2.34 (t, 3H), δ 2.22-2.19 (m, 6H), δ 1.54-1.44 (m, 4H), δ 1.18-1.15 (m, 18H), δ 0.52-0.50 (m, 4H)

Preparation Example 9: Preparation of 2-(2-(2-(2-phenoxyethoy)ethoxy)ethoxy)ethyl 3-(cyclohexyl((triethoxysilyl)methyl)amino)propanoate To a 50 ml, round-bottomed flask, 3.449 mmol of (N-cyclohexylaminomethyl)triethoxysilane and 50 ml of ethanol were added for dissolving, and 3.449 mmol of poly(ethylene glycol) phenyl ether acrylate (Sigma-Aldrich, Mn 324) was added thereto, followed by stirring at room temperature in nitrogen conditions for 8 hours. After finishing the reaction, solvents were removed under a reduced pressure and distilled at 120° C. under a reduced pressure to obtain 3.13 mmol of a 2-(2-(2-(2-phenoxyethoy)ethoxy)ethoxy)ethyl 3-(cyclohexyl((triethoxysilyl)methyl)amino)propanoate compound of Formula (ix) (Yield 91.1%). ¹H NMR spectroscopic data of separated 2-(2-(2-(2-phenoxyethoy)ethoxy)ethoxy)ethyl 3-(cyclohexyl((triethoxysilyl)methyl)amino)propanoate are as follows.

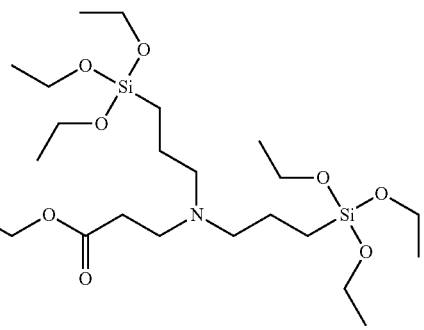

(ix)

¹H-NMR (500 MHz, CDCl₃) δ 7.26-7.24 (m, 2H), δ 6.93-6.88 (m, 3H), δ 4.18-4.16 (m, 2H), δ 4.11-4.09 (m, 3H), δ 3.85-3.80 (m, 6H), δ 3.71-3.61 (m, 12H), δ 2.76-2.72 (m, 2H), δ 2.50-2.39 (m, 3H), δ 2.10-2.09 (m, 2H), δ 1.74-1.72 (m, 4H), δ 1.58-1.59 (m, 1H) δ 1.24-1.15 (m, 12H), δ 1.03-1.00 (m, 1H)

Preparation Example 10: Preparation of 2-methoxyethyl 3-(bis(3-diethoxy(methyl)silyl)propyl)amino)propanoate To a 100 ml, round-bottomed flask, 73.03 mmol of bis(methyldiethoxysilylpropyl)amine (Gelest Co.) and 20 ml of ethanol were added for dissolving, and 73.03 mmol of ethylene glycol methyl ether acrylate (Acros Co.) was added thereto, followed by stirring at room temperature in nitrogen conditions for 8 hours. After finishing the reaction, solvents were removed under a reduced pressure and distilled at 120° C. under a reduced pressure to obtain 71.77 mmol of a 2-methoxyethyl 3-(bis(3-diethoxy(methyl)silyl)propyl)amino)propanoate compound of Formula (x) (Yield 98.327%). ¹H NMR spectroscopic data of separated 2-methoxyethyl 3-(bis(3-diethoxy(methyl)silyl)propyl)amino)propanoate are as follows.

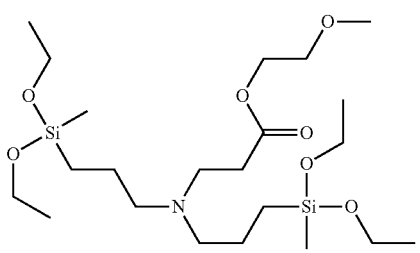

$^1$H-NMR (500 MHz, CDCl$_3$) δ 4.23-4.21 (t, 2H), δ 3.78-3.74 (m, 8H), δ3.60-3.58 (t, 2H), δ 3.39 (s, 3H), δ 2.81-2.78 (t, 2H), δ 2.49-2.46 (t, 2H), δ 2.42-2.39 (t, 3H), δ 1.51-1.45 (m, 5H), δ 1.23-1.20 (t, 18H), δ 0.57-0.54 (t, 4H), δ 0.12 (s, 6H)

Preparation Example 11: Preparation of 3-(bis(3-diethoxy(methyl)silyl)propyl)amino)propanoate To a 100 ml, round-bottomed flask, 72.99 mmol of bis(methyldiethoxysilylpropyl)amine (Gelest Co.) and 20 ml of ethanol were added for dissolving, and 72.99 mmol of ethyl acrylate (Sigma-Aldrich Co.) was added thereto, followed by stirring at room temperature in nitrogen conditions for 8 hours. After finishing the reaction, solvents were removed under a reduced pressure and distilled at 120° C. under a reduced pressure to obtain 72.18 mmol of a 3-(bis (3-diethoxy(methyl)silyl)propyl)amino)propanoate compound of Formula (xi) (Yield 98.9%). $^1$H NMR spectroscopic data of separated 3-(bis(3-diethoxy(methyl)silyl) propyl)amino)propanoate are as follows.

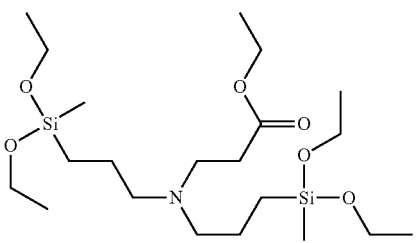

$^1$H-NMR (500 MHz, CDCl$_3$) δ 4.14-4.10 (m, 2H), δ 3.78-3.74 (m, 8H), δ 2.80-2.79 (t, 2H), δ 2.43-2.39 (m, 6H), δ 1.52-1.54 (m, 4H), δ 1.27-1.20 (m, 15H), δ 0.58-0.54 (t, 4H), δ 0.11 (s, 6H)

Example 1: Modified Styrene-Butadiene Copolymer

To a 2 L, autoclave reactor, 29.7 g of styrene, 78.1 g of 1,3-butadiene, 550 g of normal hexane, and 0.124 g of 2,2-di(2-tetrahydrofuryl)propane (DTP) as a polar additive were added, followed by elevating the temperature in the reactor to 50° C. The temperature in the reactor reached 50° C., 3 mmol of n-butyllithium was added to the reactor, followed by performing an adiabatic and heating reaction. After about 20 minutes, 2.2 g of 1,3-butadiene was added for capping the terminal of SSBR with butadiene. After 5 minutes, 0.181 g of 2-methoxyethyl 3-(bis(3-triethoxysilyl) propyl)amino)propanoate prepared in Preparation Example 7 was added and reacted for 15 minutes ([DTP]/[act. Li]=2.3, [modifier]/[act. Li]=1.0). After that, a polymerization reaction was stopped using ethanol, and 4.5 ml of a solution in which 0.3 wt % of butylated hydroxytoluene (BHT) as an antioxidant was dissolved in hexane was added. As a result, the polymer thus obtained was added to warm water heated using steam and stirred to remove solvents. Remaining solvents and water were removed by roll drying to prepare a modified conjugated diene copolymer.

Example 2

To a 20 L, autoclave reactor, 270 g of styrene, 710 g of 1,3-butadiene, 5 kg of normal hexane, and 0.94 g of 2,2-di (2-tetrahydrofuryl)propane (DTP) as a polar additive were added, followed by elevating the temperature in the reactor to 40° C. The temperature in the reactor reached 40° C., 25.40 g (2.62 wt % in hexane, 33% activation) of n-butyl-lithium was added to the reactor, followed by performing an adiabatic and heating reaction. After about 20 minutes, 20.0 g of 1,3-butadiene was added for capping the terminal of SSBR with butadiene. After 5 minutes, 1.98 g of an ethyl 3-(bis(3-triethoxy(methyl)silyl)propyl)amino)propanoate modifier prepared in Preparation Example 11 was added and reacted for 15 minutes ([DTP]/[act. Li]=1.46, [modifier]/ [act. Li]=0.85). After that, a polymerization reaction was stopped using ethanol, and 33 g of a solution in which 30 wt % of Wingstay K as an antioxidant was dissolved in hexane was added. As a result, the polymer thus obtained was added to warm water heated using steam and stirred to remove solvents. Remaining solvents and water were removed by roll drying to prepare a modified conjugated diene copolymer.

Comparative Example

A modified conjugated diene copolymer was prepared by performing the same procedure described in Example 1 except for using N,N-bis(triethoxysilylpropyl)piperazine as the modifier.

Experimental Example 1

Weight average molecular weight (Mw), number average molecular weight (Mn), molecular weight distribution (MWD), maximum peak molecular weight (Mp), combination efficiency (%) and pattern viscosity (MV) were measured for the modified conjugated diene copolymers prepared in Example 1, Example 2 and Comparative Example. The results are shown in the following Table 1.

The weight average molecular weight (Mw), the number average molecular weight (Mn), and the maximum peak molecular weight (Mp) were measured via gel permeation chromatography (GPC) analysis, and the molecular weight distribution (MWD, Mw/Mn) and the combination efficiency (%) were obtained by calculating using each molecular weight thus measured. In particular, for GPC, two columns of PLgel Olexis (Polymer Laboratories Co.) and one column of PLgel mixed-C (Polymer Laboratories Co.) were in combination, and polystyrene (PS) was used as a GPC standard material for calculating the molecular weight.

TABLE 1

| Division | Mn (g/mol, ×10⁴) | Mw (g/mol, ×10⁴) | Mp (g/mol, ×10⁴) | Combination efficiency (%) | Molecular weight distribution (Mw/Mn) |
|---|---|---|---|---|---|
| Example 1 | 49 | 120 | 35 | 38 | 2.4 |
|  |  |  | 77 | 28 |  |
|  |  |  | 124 | 34 |  |
| Example 2 | 27 | 42 | 30 | 40 | 1.4 |
|  |  |  | 64 | 60 |  |
| Comparative Example | 34 | 45 | 25 | 43 | 1.3 |
|  |  |  | 53 | 57 |  |

As shown in the above Table 1, the modified styrene-butadiene copolymers of Examples 1 and 2, prepared using the modifiers according to the present invention have markedly increased combination efficiency of a polymer component when compared to the modified styrene-butadiene copolymer of Comparative example, which was prepared using the conventional modifier.

In particular, when comparing the modified styrene-butadiene copolymer of Example 1 with the modified styrene-butadiene copolymer of Comparative Example, the combination efficiency (62%, in the case that Mp was 77×10⁴ and 124×10⁴) of the polymer component of the modified styrene-butadiene copolymer of Example 1 increased by 2.7 times when compared to the combination efficiency (57%, in the case that Mp was 53×10⁴) of the polymer component of the styrene-butadiene copolymer of Comparative Example, and the molecular weight was high for the modified styrene-butadiene copolymer of Example 1.

The increase of the molecular weight even with the same number of triethoxysilane groups in the modifier means that a highly modified polymer was produced by increasing reactivity by introducing a polymer an active part and an ester group having high reactivity to the modifier according to the present invention when compared to the conventional modifier. In addition, for Example 2, the combination efficiency of the polymer component was increased (60%) with high modification efficiency even though the amount used of the modifier was 77% relative to the amount used of the modifier of Comparative Example. From the results, as shown in FIG. 1, the active part (—Li⁺) of a copolymer combined with a metal may be combined with oxygen in the ethylene glycol of the modifier, and the reactivity of anions may increase, the reaction rate may increase, and the modification reaction may become easy, thereby increasing the combination efficiency of the polymer component as described above.

The invention claimed is:

1. A modified styrene-butadiene copolymer comprising a functional group derived from a modifier represented by the following Formula 1:

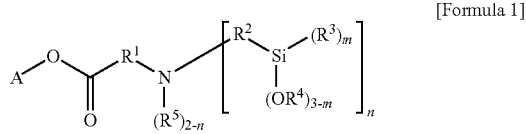

[Formula 1]

in the above Formula 1,

A is a hydrocarbon of 1 to 20 carbon atoms, or a hydrocarbon of 1 to 20 carbon atoms, comprising at least one heteroatom selected from the group consisting of N, S and O, $R^1$ and $R^2$ are each independently a substituted or unsubstituted divalent hydrocarbon of 1 to 20 carbon atoms, the substituted hydrocarbon being substituted with at least one substituent selected from the group consisting of an alkyl of 1 to 20 carbon atoms, a cycloalkyl of 3 to 20 carbon atoms and an aryl of 6 to 30 carbon atoms, $R^3$ to $R^5$ are each independently a monovalent hydrocarbon having 1 to 20 carbon atoms, m is an integer from 0 to 3, and n is an integer of 1 or 2, wherein in the case where A is the hydrocarbon of 1 to 20 carbon atoms, n is an integer of 2.

2. The modified styrene-butadiene copolymer of claim 1, wherein

A is selected from the group consisting of an alkyl of 1 to 20 carbon atoms, a cycloalkyl of 3 to 20 carbon atoms, an aryl of 6 to 20 carbon atoms, an arylalkyl of 7 to 20 carbon atoms, an alkoxy of 1 to 20 carbon atoms, an alkoxyalkyl of 2 to 20 carbon atoms, a phenoxyalkyl of 7 to 20 carbon atoms, an aminoalkyl of 1 to 20 carbon atoms, and $[R^{11}O]_xR^{12}$, wherein $R^{11}$ is an alkylene of 2 to 10 carbon atoms, $R^{12}$ is selected from the group consisting of a hydrogen atom, an alkyl of 1 to 10 carbon atoms, a cycloalkyl of 3 to 12 carbon atoms, an aryl of 6 to 16 carbon atoms, and an arylalkyl of 7 to 16 carbon atoms, and x is an integer from 2 to 10.

3. The modified styrene-butadiene copolymer of claim 1, wherein

A is selected from the group consisting of an alkyl of 1 to 10 carbon atoms, a cycloalkyl of 3 to 12 carbon atoms, an aryl of 6 to 12 carbon atoms, an arylalkyl of 7 to 12 carbon atoms, an alkoxyalkyl of 2 to 10 carbon atoms, a phenoxyalkyl of 7 to 12 carbon atoms, an aminoalkyl of 1 to 10 carbon atoms, and $-[R^{11}O]_xR^{12}$, wherein $R^{11}$ is an alkylene of 2 to 10 carbon atoms, $R^{12}$ is selected from the group consisting of a hydrogen atom, an alkyl of 1 to 10 carbon atoms, a cycloalkyl of 3 to 12 carbon atoms, an aryl of 6 to 16 carbon atoms, and an arylalkyl of 7 to 16 carbon atoms, and x is an integer from 2 to 10, $R^1$ and $R^2$ are each independently an alkylene of 1 to 5 carbon atoms, $R^3$ and $R^4$ are each independently an alkyl of 1 to 5 carbon atoms, $R^5$ is an alkyl of 1 to 5 carbon atoms, or a cycloalkyl of 3 to 8 carbon atoms, m is an integer from 0 to 2, and n is an integer of 1 or 2, in the case where A is the alkyl of 1 to 10 carbon atoms, the cycloalkyl of 3 to 12 carbon atoms, the aryl of 6 to 12 carbon atoms, or the arylalkyl of 7 to 12 carbon atoms, n is an integer of 2.

4. The modified styrene-butadiene copolymer of claim 1, wherein

A is one selected from the group consisting of an alkyl of 1 to 10 carbon atoms, an alkoxyalkyl of 2 to 10 carbon atoms and a phenoxyalkyl of 7 to 12 carbon atoms, $R^1$ and $R^2$ are each independently an alkylene of 1 to 5 carbon atoms, $R^3$ and $R^4$ are each independently an alkyl of 1 to 5 carbon atoms, m is an integer of 0 or 1, and n is an integer of 2.

5. The modified styrene-butadiene copolymer of claim 1, wherein the modifier is at least one selected from the group consisting of 2-phenoxyethyl 3-(cyclohexyl((triethoxysilyl)

methyl)amino)propanoate, 2-methoxyethyl 3-(cyclohexyl ((triethoxysilyl)methyl)amino)propanoate, 2-(dimethylamino)ethyl 3-(cyclohexyl((triethoxysilyl)methyl)amino) propanoate, 2,5,8,11,14,17,20,23,26-nonaoxaoctacosane-28-yl 3-(bis(3-(triethoxysilyl)propyl)amino)propanoate, 2-(2-(2-(2-phenoxyethoxy)ethoxy)ethyl 3-(bis(3-(triethoxysilyl)propyl)amino)propanoate, 2-phenoxyethyl 3-(bis(3-(triethoxysilyl)propyl)amino)propanoate, 2-methoxyethyl 3-(bis(3-(triethoxysilyl)propyl)amino)propanoate, 2-(dimethylamino)ethyl 3-(bis(3-(triethoxysilyl) propyl)amino)propanoate, 2-(2-(2-(2-phenoxyethoxy) ethoxy)ethyl 3-(cyclohexyl((triethoxysilyl)methyl) amino)propanoate, 2-methoxyethyl 3-(bis(3-(diethoxy (methyl)silyl)propyl)amino)propanoate and ethyl 3-(bis(3-(diethoxy(methyl)silyl)propyl)amino)propanoate.

6. The modified styrene-butadiene copolymer of claim 1, wherein the copolymer has a number average molecular weight of 1,000 g/mol to 2,000,000 g/mol.

7. The modified styrene-butadiene copolymer of claim 1, wherein the copolymer has a molecular weight distribution (Mw/Mn) of 1.05 to 10.

8. The modified styrene-butadiene copolymer of claim 1, wherein the copolymer has a vinyl content of 5 wt % or more.

9. A method of preparing a modified styrene-butadiene copolymer according to claim 1, the method comprising:
   1) preparing an active polymer combined with an alkali metal by polymerizing an aromatic vinyl monomer and a conjugated diene monomer in the presence of an organometallic compound in a hydrocarbon solvent; and
   2) reacting the active polymer with a modifier represented by the following Formula 1:

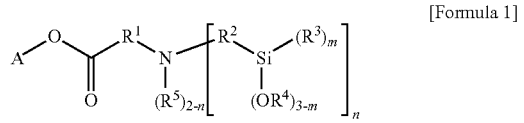

[Formula 1]

in Formula 1,
A is a hydrocarbon of 1 to 20 carbon atoms, or a hydrocarbon of 1 to 20 carbon atoms, comprising at least one heteroatom selected from the group consisting of N, S and O,
$R^1$ and $R^2$ are each independently a substituted or unsubstituted divalent hydrocarbon of 1 to 20 carbon atoms, the substituted hydrocarbon being substituted with at least one substituent selected from the group consisting of an alkyl of 1 to 20 carbon atoms, a cycloalkyl of 3 to 20 carbon atoms and an aryl of 6 to 30 carbon atoms,
$R^3$ to $R^5$ are each independently a monovalent hydrocarbon having 1 to 20 carbon atoms,
m is an integer from 0 to 3, and n is an integer of 1 or 2, wherein in the case where A is the hydrocarbon of 1 to 20 carbon atoms, n is an integer of 2.

10. The method of preparing a modified styrene-butadiene copolymer of claim 9, wherein the organometallic compound is employed in an amount ratio of 0.01 mmol to 10 mmol based on 100 g of a total amount of the aromatic vinyl monomer and the conjugated diene monomer.

11. The method of preparing a modified styrene-butadiene copolymer of claim 9, wherein the organometallic compound is methyllithium, ethyllithium, propyllithium, n-butyllithium, s-butyllithium, t-butyllithium, hexyllithium, n-decyllithium, t-octyllithium, phenyllithium, n-eicosyllithium, 4-butylphenyllithium, 4-tolyllithium, cyclohexyllithium, 3,5-di-n-heptylcyclohexyllithium, 4-cyclopentyllithium, naphthyllithium, naphthylsodium, naphthylpotassium, lithium alkoxide, sodium alkoxide, potassium alkoxide, lithium sulfonate, sodium sulfonate, potassium sulfonate, lithium amide, sodium amide, potassium amide or lithium isopropylamide.

12. The method of preparing a modified styrene-butadiene copolymer of claim 9, wherein the polymerization in step 1) is performed after further adding a polar additive.

13. The method of preparing a modified styrene-butadiene copolymer of claim 12, wherein the polar additive is employed in an amount ratio of 0.001 g to 10 g relative to 1 mmol of a total amount of the organometallic compound.

14. The method of preparing a modified styrene-butadiene copolymer of claim 9, wherein the modifier represented by Formula 1 is at least one selected from the group consisting of 2-phenoxyethyl 3-(cyclohexyl((triethoxysilyl)methyl) amino)propanoate, 2-methoxyethyl 3-(cyclohexyl((triethoxysilyl)methyl)amino)propanoate, 2-(dimethylamino)ethyl 3-(cyclohexyl((triethoxysilyl)methyl)amino)propanoate, 2,5,8,11,14,17,20,23,26-nonaoxaoctacosane-28-yl 3-(bis(3-(triethoxysilyl)propyl)amino)propanoate, 2-(2-(2-(2-phenoxyethoxy)ethoxy)ethyl 3-(bis(3-(triethoxysilyl) propyl)amino)propanoate, 2-phenoxyethyl 3-(bis(3-(triethoxysilyl)propyl)amino)propanoate, 2-methoxyethyl 3-(bis(3-(triethoxysilyl)propyl)amino)propanoate, 2-(dimethylamino)ethyl 3-(bis(3-(triethoxysilyl)propyl)amino)propanoate, 2-(2-(2-(2-phenoxyethoxy)ethoxy)ethyl 3-(cyclohexyl((triethoxysilyl)methyl)amino)propanoate, 2-methoxyethyl 3-(bis(3-(diethoxy(methyl)silyl)propyl) amino)propanoate and ethyl 3-(bis(3-(diethoxy(methyl)silyl)propyl)amino)propanoate.

15. The method of preparing a modified styrene-butadiene copolymer of claim 9, wherein the modifier represented by Formula 1 is employed in an amount ratio of 0.1 mol to 10 mol relative to 1 mol of the organometallic compound.

16. A modifier having a structure of the following Formula 1:

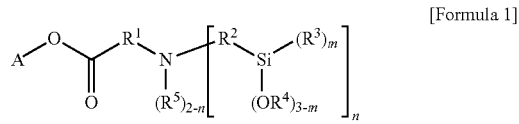

[Formula 1]

in Formula 1,
A is selected from the group consisting of a cycloalkyl of 3 to 20 carbon atoms, an aryl of 6 to 20 carbon atoms, an arylalkyl of 7 to 20 carbon atoms, an alkoxy of 1 to 20 carbon atoms, an alkoxyalkyl of 2 to 20 carbon atoms, a phenoxyalkyl of 7 to 20 carbon atoms, an aminoalkyl of 1 to 20 carbon atoms, and —$[R^{11}O]_xR^{12}$, where $R^{11}$ is an alkylene of 2 to 10 carbon atoms, $R^{12}$ is selected from the group consisting of a hydrogen atom, an alkyl of 1 to 10 carbon atoms, a cycloalkyl of 3 to 12 carbon atoms, an aryl of 6 to 16 carbon atoms, and an arylalkyl of 7 to 16 carbon atoms, and x is an integer from 2 to 10,
$R^1$ and $R^2$ are each independently a substituted or unsubstituted divalent hydrocarbon of 1 to 20 carbon atoms, the substituted hydrocarbon being substituted with at least one substituent selected from the group consisting of an alkyl of 1 to 20 carbon atoms, a cycloalkyl of 3 to 20 carbon atoms and an aryl of 6 to 30 carbon atoms, $R^3$ to $R^5$ are each independently a monovalent hydrocarbon having 1 to 20 carbon atoms, m is an integer from 0 to 3, and n is an integer of 1 or 2, wherein in the case where A is the hydrocarbon of 1 to 20 carbon atoms, n is an integer of 2.

17. The modifier of claim 16, wherein $R^1$ and $R^2$ are each independently an alkylene of 1 to 5 carbon atoms, $R^3$ to $R^5$ are each independently an alkyl of 1 to 5 carbon atoms, m is an integer of 0 or 1, and n is an integer of 2.

18. The modifier of claim 16, wherein the modifier is for modifying a styrene-butadiene copolymer.

19. A method of preparing a modifier according to claim 16, the method comprising a step of reacting a compound of the following Formula 2 and a compound of the following Formula 3:

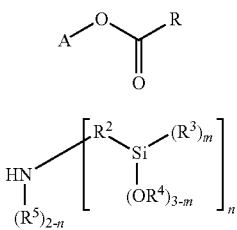

[Formula 2]

[Formula 3]

in Formulae 2 and 3,

A is selected from the group consisting of a cycloalkyl of 3 to 20 carbon atoms, an aryl of 6 to 20 carbon atoms, an arylalkyl of 7 to 20 carbon atoms, an alkoxy of 1 to 20 carbon atoms, an alkoxyalkyl of 2 to 20 carbon atoms, a phenoxyalkyl of 7 to 20 carbon atoms, an aminoalkyl of 1 to 20 carbon atoms, and —$[R^{11}O]_xR^{12}$, wherein $R^{11}$ is an alkylene of 2 to 10 carbon atoms, $R^{12}$ is selected from the group consisting of a hydrogen atom, an alkyl of 1 to 10 carbon atoms, a cycloalkyl of 3 to 12 carbon atoms, an aryl of 6 to 16 carbon atoms, and an arylalkyl of 7 to 16 carbon atoms, and x is an integer from 2 to 10, R is a substituted or unsubstituted alkenyl of 2 to 20 carbon atoms, the substituted alkenyl being substituted with a substituent selected from the group consisting of an alkyl of 1 to 20 carbon atoms, a cycloalkyl of 3 to 20 carbon atoms and an aryl of 6 to 30 carbon atoms, $R^2$ is a substituted or unsubstituted divalent hydrocarbon of 1 to 20 carbon atoms, the substituted hydrocarbon being substituted with a substituent selected from the group consisting of an alkyl of 1 to 20 carbon atoms, a cycloalkyl of 3 to 20 carbon atoms and an aryl of 6 to 30 carbon atoms, $R^3$ to $R^5$ are each independently a hydrocarbon of 1 to 20 carbon atoms, m is an integer from 0 to 3, and n is an integer of 1 or 2, wherein in the case where A is the hydrocarbon of 1 to 20 carbon atoms, n is an integer of 2.

20. The method of preparing a modifier of claim 19, wherein 0.01 to 0.2 mol of the compound of Formula 3 is employed relative to 1 mol of the compound of Formula 2.

* * * * *